United States Patent [19]

Breillatt, Jr. et al.

[11] Patent Number: 5,510,115
[45] Date of Patent: Apr. 23, 1996

[54] METHOD AND COMPOSITION FOR ADMINISTRATION OF BENEFICIAL AGENT BY CONTROLLED DISSOLUTION

[75] Inventors: Julian P. Breillatt, Jr., Mundelein; Lecon Woo; Deanna J. Nelson, both of Libertyville; Richard Appl, Downer's Grove; Naomi L. Weinless, Highland Park; Sharon Pokropinski, Berwyn; Paul Soltys, Palatine; Sumner A. Barenberg, Chicago, all of Ill.

[73] Assignee: Baxter Travenol Laboratories, Inc., Deerfield, Ill.

[21] Appl. No.: 351,971

[22] Filed: Dec. 8, 1994

Related U.S. Application Data

[60] Continuation of Ser. No. 80,399, Jun. 21, 1993, abandoned, which is a division of Ser. No. 345,334, May 1, 1989, abandoned, which is a continuation-in-part of Ser. No. 120,892, Nov. 16, 1987, abandoned, and a continuation-in-part of Ser. No. 121,316, Nov. 16, 1987, abandoned.

[51] Int. Cl.$^6$ ................................................ A61K 9/22
[52] U.S. Cl. ..................... 424/473; 424/422; 424/426; 604/56; 604/85; 604/92
[58] Field of Search ............................ 424/473, 422, 424/426; 604/56, 85, 92

[56] References Cited

U.S. PATENT DOCUMENTS

| Re. 25,129 | 2/1962 | Walter | 128/214 |
|---|---|---|---|
| D. 229,049 | 11/1973 | Tablet | 424/15 |
| 1,541,744 | 2/1924 | Wiseman | 514/777 |
| 2,987,445 | 6/1961 | Levesque | 167/82 |
| 2,996,431 | 8/1961 | Barry | 167/82 |
| 3,365,365 | 1/1968 | Butler et al. | 167/82 |
| 3,558,768 | 12/1969 | Klippel | 424/21 |
| 3,874,384 | 4/1975 | Deindoerfer et al. | 604/408 |
| 3,965,896 | 6/1976 | Swank | 128/214 R |
| 3,993,066 | 11/1976 | Viraq | 128/214 |
| 4,086,924 | 5/1978 | Latham | 604/6 |
| 4,130,647 | 12/1978 | Taylor | 424/251 |
| 4,134,943 | 1/1979 | Knitsch et al. | 264/28 |
| 4,235,236 | 11/1980 | Theeuwes | 128/260 |
| 4,257,426 | 3/1981 | Bailey | 128/766 |
| 4,381,776 | 5/1983 | Latham | 604/317 |
| 4,395,260 | 7/1983 | Todd et al. | 604/122 |
| 4,511,351 | 4/1985 | Theeuwes | 604/56 |
| 4,511,352 | 4/1985 | Theeuwes | 604/56 |
| 4,511,353 | 4/1985 | Theeuwes | 604/85 |
| 4,552,555 | 11/1985 | Theeuwes | 604/56 |
| 4,623,334 | 11/1986 | Riddell | 604/85 |
| 4,684,516 | 8/1987 | Bhutani | 424/469 |
| 4,685,918 | 8/1987 | Amidon et al. | 604/892 |
| 4,728,668 | 4/1988 | Bellotti et al. | 604/238 |
| 4,753,800 | 6/1988 | Mozda | 424/440 |
| 4,758,430 | 7/1988 | Sabin | 424/94.1 |
| 4,769,318 | 9/1988 | Hamasaki et al. | 435/2 |

FOREIGN PATENT DOCUMENTS

| 59694 | 9/1982 | European Pat. Off. |
|---|---|---|
| 0192367 | 8/1986 | European Pat. Off. |
| 1108782 | 1/1956 | France. |
| 497181 | 9/1969 | Switzerland. |
| 982107 | 2/1965 | United Kingdom. |
| 1476057 | 6/1977 | United Kingdom. |
| 2054599 | 2/1981 | United Kingdom. |
| 1595388 | 8/1981 | United Kingdom. |
| 8600004 | 1/1986 | WIPO. |

OTHER PUBLICATIONS

Myhre, et al., "Red Cell Antigen Persistence", *Transfusion*, vol. 24, No. 6, pp. 499–501 (1984).

*Primary Examiner*—D. Gabrielle Phelan
*Attorney, Agent, or Firm*—Hill, Steadman & Simpson

[57] ABSTRACT

An anhydrous solid water-soluble composition and method for direct controlled administration of beneficial agents to a flowing medical fluid. The beneficial agents are geometrically dispersed in a solid matrix and isolated from one and other to allow administration of mutually reactive agents.

16 Claims, No Drawings

METHOD AND COMPOSITION FOR ADMINISTRATION OF BENEFICIAL AGENT BY CONTROLLED DISSOLUTION

CROSS-REFERENCE TO RELATED APPLICATIONS

This is a continuation of application Ser. No. 08/080,399, filed on Jun. 21, 1993, now abandoned, which is a Divisional of Ser. No. 345,334, filed May 1, 1989, now abandoned, which is in turn a Continuation-in-Part of application Ser. Nos. 120,892 and 121,316, both filed Nov. 16, 1987, now abandoned.

FIELD OF THE INVENTION

The present invention relates to delivery of beneficial agents to flowing fluids. More specifically, this invention pertains to predetermined, controlled and variable delivery of beneficial agents to a flowing medical fluid, which agents may be otherwise insoluble or unstable in the medical fluid.

BACKGROUND OF THE INVENTION

Parenteral delivery and collection of medical fluids are important factors in current medical care. Such fluids are delivered principally via intravenous and intraperitoneal routes, while phlebotomy constitutes the major collection modality. Intravenous fluids commonly include blood and blood fractions, sugar, electrolyte and osmotic solutions, and nutrient preparations. Fluids are generally delivered intraperitoneally to remove excreted nitrogenous wastes from end stage renal disease patients in a process known as peritoneal dialysis.

Many beneficial and therapeutic agents are preferably delivered via parenteral fluids to avoid digestive tract and liver associated modification of those agents. Historically such agents have been formulated and added to the parenteral fluid reservoir by a pharmacist or nurse. Because this is a labor intensive step with opportunity for error, and because many beneficial agents are less stable in solution than in dry form, systems have been developed to facilitate formulation of soluble dry agents with parenteral fluid immediately before use. One such system disclosed in U.S. Pat. No. 4,614,267 still requires manual formulation.

The next advance provided preprogrammed, unattended systems to formulate parenteral fluid with soluble dry agents in situ in a formulation chamber associated with the primary delivery set. An example of such a system is disclosed in U.S. Pat. No. 4,552,555 in which the beneficial agent is contained within a formulation chamber bounded by a membrane. The membrane serves to control the delivery rate of beneficial agent into the flowing stream of medical fluid. Controlled delivery of a beneficial agent into a medical fluid can also be achieved through diffusion of the agent from a non-erodible polymer matrix that contains and serves as a reservoir of the agent. Generally the permeability of the matrix controls the diffusion rate of the agent into the surrounding environment. Such systems are described in U.S. Pat. Nos. 3,921,636 and 4,511,353. When a membrane or matrix system is used to control beneficial agent delivery into parenteral fluids, actual delivery rate of the agent to the patient is substantially independent of fluid flow rate; a benefit if adequate fluid flow control means are not available. However, that same flow rate independence restricts the ability of the healthcare professional to increase dose rate to meet patient needs. While such inventions have improved the efficiency and safety of administering beneficial agents to parenteral fluids, they fall short of the ideal: (1) by not providing a clear visual indication that the dose has been delivered; 2) by causing a major portion of the beneficial agent in the formulation chamber to dissolve in the parenteral fluid early in the delivery procedure, thereby leaving the agent in solution for the extended period of time required to deliver the dose; and, (3) by requiring that the agent for formulation be present in a form which is soluble in the parenteral fluid.

The ideal system for parenteral or blood delivery would be a matrix that contains and/or protects, as necessary, one or more entrapped beneficial agents in a dry, stable state; that, when placed in a flow chamber in the medical fluid administration line, disappears as the agent is delivered into the flowing stream, indicating delivery of the dose. The simplest means of effecting disappearance is dissolution of the matrix in the stream of medical fluid, thereby releasing the entrapped agent. This suggests the matrix should be formed from innocuous components clinically acceptable for use in parenteral fluids and could be the beneficial agent itself or a component thereof, a beneficial metabolite, or a non-toxic excretable molecule.

Preferably, the matrix would dissolve proportionally to the flow of medical fluid over its surface with its dissolution rate determining the delivery rate of the beneficial agent; thus allowing the beneficial agent to remain stable and protected within the matrix until both matrix and agent become hydrated and dissolve. The dissolution rate of the beneficial agent should match or exceed the dissolution rate of the matrix; otherwise the matrix could dissolve away leaving the beneficial agent as an insoluble mass in the flowing fluid.

Since the most stable forms of many drugs are not directly soluble in water or saline, it would be advantageous to use them as the storage form in the matrix, co-entrapped with dry modifying agents, such as pH buffers or solubilizing reactants, under conditions that they neither react with each other during the formation of the matrix nor during storage, but such that when the dissolving fluid reaches the beneficial agent, it will have dissolved sufficient pH buffer or reactant to create a localized environment in the fluid boundary layer that favors dissolution of the otherwise insoluble beneficial agent.

A similar rationale leads to matrix compositions that deliver active agents from inactive storage forms co-entrapped with their activator species; or, as examples of other variations, beneficial agents in their active forms co-entrapped with inhibitors of enzymes that would inactivate the agents, and, initial release of a beneficial agent followed in time by the release of its inactivator. The latter case may be achieved, for example, by forming the matrix with the separate agents in defined concentric layers. The matrix may also serve as a separator of mutually reactive species. In such a case, the matrix must be appropriately inert in a chemical sense towards the beneficial agents and the reactants associated with them.

In summary, controlled dissolution operates at five different levels to provide controlled administration of beneficial agents to flowing medical fluids: (1) the flow field of the medical fluid in conjunction with the shape of the solid matrix element, (2) the dissolution properties of the matrix material, (3) the geometric distribution pattern of beneficial agent and modifying agent particles within the matrix, (4) the dissolution properties and size of beneficial agent and modifying agent particles, and (5) the chemical/solubilizing interactions between beneficial agents and modifying agents at the solid/fluid interface.

While each beneficial agent or combination of such agents may require individual adjustment for optimum matrix composition and method of formation, general principles are available. It is well known that essential oils with extreme sensitivity to heat, light, air and moisture can be stabilized for storage in dry form by encapsulation in dry sugar melts using methods disclosed by Swisher in U.S. Pat. Nos. 2,809,895 and 3,041,180. Similarly, therapeutic activity of heat sensitive beneficial agents can be preserved by incorporating them at moderate temperatures into a cooling melt of the embedding matrix using standard candy manufacture methods such as those disclosed by Mozda in U.S. Pat. No. 4,753,800. Sair, in choosing a protective and stabilizing matrix material for encapsulated food additives, disclosed in U.S. Pat. No. 4,232,047 that mustard oil was less reactive with a matrix composed of polymeric carbohydrate than with a protein matrix. Analogous reasoning when choosing initial matrix materials for parenteral fluids might suggest use of non-reducing monomeric carbohydrates. Water may be the most chemically active molecule in a matrix, and stability of certain beneficial agents could require rigorous exclusion of reactive water from their encapsulating matrix, even below the 0.5 to 2.0% water content values considered virtually anhydrous by Swisher in U.S. Pat. No. 3,041,180.

SUMMARY OF THE INVENTION

The present invention provides an anhydrous, solid, water soluble composition for the direct controlled administration of beneficial agents to a flow of medical fluid. The composition includes a matrix which is soluble in the medical fluid and in which the beneficial agent or agents are dispersed.

The agents may be dispersed in such a way as to control their administration into the fluid flow by controlling the rate of dissolution of the matrix. In other words, the rate of administration of the beneficial agent into the stream of fluid may be made to correspond to the rate of dissolution of the matrix. The agents may also be dispersed in such a way as to isolate agents from one another until the moment of release into the fluid. This is desirable in situations such as, for example; (1) where one might wish to isolate mutually reactive agents from one another; or, (2) store an agent in the matrix in an insoluble, inactive form and include within the matrix a solubilizer and activator which, upon dissolution of the matrix, will solubilize and activate the agent as it is being administered.

DESCRIPTION OF THE INVENTION

The present invention provides an anhydrous, solid, water-soluble, particulate composition for dissolution-controlled administration of beneficial agents to medical fluids. It includes a matrix, preferably comprising one or more sugars or sugar alcohols in anhydrous solidified melt form. The beneficial agent or agents are distributed in particulate form and in predetermined pattern within the matrix. Chemical species that modify the beneficial agents or modulate their action or delivery also may be dispersed in particulate form within the matrix. Fabrication methods may be chosen such that each particle is surrounded by, and isolated from other particles by the continuous phase of the matrix substance.

For use this composition is made into solid formed elements whose external shape and geometry partially determine the relative dissolution rate of their various surfaces in a flowing stream of medical fluid. The disappearance of the composition provides a visual indicator of delivery of the beneficial agent into the stream of medical fluid.

The present invention allows the healthcare practitioner a tremendous amount of flexibility in delivering parenterally to a patient agents which were heretofore otherwise difficult or impossible to deliver because they were insoluble, had very limited shelf-life, were incompatible with one another, etc.

More specifically, the present invention tremendously simplifies the parenteral administration of:

1. water-insoluble beneficial agents; the beneficial agents may be stored in the matrix in water-insoluble form along with modifying agents or species which cause the beneficial agents to become water-soluble, and therefore, administrable parenterally as the matrix dissolves in the flowing medical fluid.
2. activated beneficial agents; the beneficial agents with a short shelf life may be stored in the matrix in inactive form along with modifying species which activate the beneficial agents as the matrix dissolves and exposes the agent to the modifier.
3. beneficial agents and modifying or modulating agents in predetermined, concurrent and/or sequential manner; the various agents may be distributed in the matrix, each in a specific geometric pattern whose proximity to the dissolving edge of the solid element determines the relative times of their dissolution and their time-based concentration profiles in the flowing medical fluid.
4. easily inactivated beneficial agents; the beneficial agents may be stored in the matrix along with modulating species, which upon dissolution into the medical fluid act to extend the active lifetime of the beneficial agents by inhibiting potentially inactivating enzymes or factors present in the medical fluid and/or body fluid to which the agent is ultimately delivered.
5. a beneficial agent and its inactivator or its antagonist released sequentially; the beneficial agent and its inactivator or its antagonist mat be stored in the matrix in separate particulate form and in specific geometric distributions that provide sequential release into the flowing stream of medical fluid, which allows the beneficial agent to reach its site of action and act, then either be inactivated or have its action modulated by its antagonist before the beneficial agent can act on other sites where its action is undesirable.

The present invention is made possible in large part by a boundary layer phenomenon. More specifically, both the fine structure of the particulate composition and the shape of the formed element play important roles in its delivery function by providing a dynamic formulation and reaction region that includes the solid matrix/fluid boundary layer interface where insoluble and/or inactive beneficial agent precursors may be transformed into pharmaceutically acceptable forms in an unattended, predetermined manner not requiring artificial diffusion limiting devices such as membranes or polymeric matrices.

By example, the flow of medical fluid past the surface of the formed element generally establishes an unmixed fluid boundary layer at the solid/fluid interface. As the particulate composition dissolves in the fluid, the matrix components, beneficial agents and modifying agents accumulate in the boundary layer, then diffuse into the flowing stream. Chemical reactions previously prevented by physical separation of particulates in the solid matrix now occur in this concentrated boundary layer, both between two soluble species and between insoluble species exposed at the solid interface by dissolution of the matrix and soluble species.

Since the geometry, state and size of the solid formed element of particulate composition can be controlled by the method of fabrication, both constant and variable predetermined dissolution rates of the element can be obtained at constant fluid flow rate. Specifically, an element may be provided that is relatively long and wide with respect to its thickness. With such a configuration there is little change in surface area as the element dissolves, so that the dissolution rate remains substantially uniform, at least until the element nears exhaustion. By appropriately shaping the element, for example, into a cylinder, or a structure with multiple flow channels, variable dissolution regimes may be obtained.

The particulate composition of this invention preferably may be manufactured by dispersion of dry, powdered beneficial agents and modifying species into a dry, water soluble fluid phase material and thereafter allowing the dispersion thus formed to assume a solid state. The fluid phase material shall preferably include a molten sugar or a mixture of molten sugars, and optionally, soluble, heat stable, chemical species compatible with the included particulate beneficial agents. The powdered or particulate beneficial agents and modifying species are preferably dispersed in the fluid phase material after it has cooled from a melt, but while it still retains sufficient fluidity to allow inclusion of the particles. Dispersion of the beneficial agents may be effected by mixing in its various forms, or preferably by well known cooker-extruder processes wherein one may pass directly from dry materials to a final product containing a predetermined geometric distribution of the beneficial agent within the body of the solid formed elements.

Vigorous mixing of powdered admixtures into fluid cooling melts generally causes each solid particle to be coated with the continuous fluid phase, thereby isolating the various particles from each other. Moreover, dry powdered mixtures of mutually reactive beneficial agents and/or modifying species generally may be embedded in the dry, fluid cooling melt without reaction. In a case where it is necessary that the mutually reactive beneficial agents and other species be rigorously excluded from contacting each other, they may be admixed separately and sequentially into the cooling melt.

The term sugar for the purpose of this invention shall include, singly and in combination, monosaccharides or polymers and derivatives thereof having a degree of polymerization of preferably about 1 or 2, but optionally up to the hundreds. The term sugar also includes, singly and in combination, the corresponding sugar alcohols and polymers thereof. Preferably, a sugar for use herein may include one or a combination of glucose, fructose, mannose, lactose, sucrose, trehalose, sorbitol, mannitol, xylitol, glycerol, lycasin, dextran, starch, hydroxyethyl starch, and the like.

The solidified melt of sugars that constitutes the matrix of the particulate composition may assume various physical forms depending on the combination of sugars used, the conditions of preparation, and the nature of the particulate inclusions embedded therein. It is expected that glassy, amorphous non-crystalline regions may occur in conjunction with both bulk macrocrystalline and microcrystalline regions. Where predominantly glassy morphology is desired, bulk sugars such an sorbitol and glucose may be plasticized by agents such as xylitol, glycerol or water.

For purposes of the present invention, substantially anhydrous matrix composition shall be understood to mean less than 2% water content and preferably less than 1% water. However, for certain beneficial agents that are unstable in the presence of even small amounts of water, matrix compositions containing about 0.1% water are readily achievable and employed in the present invention.

Specific examples of methods by which solid sugar matrix material may be prepared for inclusion of particulate beneficial agents include boiling sugar solutions to such temperatures as is required to achieve less than 1% water content, or by melting sugars with or without a plasticizing agent such as water or glycerol. For example, a sorbitol solution boiled to 195° C. at atmospheric pressure contains about 1% water; whereas anhydrous sorbitol melted in an oven at 150° C. alone or with 1% anhydrous glycerol can contain about 0.1% water content.

The following illustrative examples are offered to describe the advantages of the present invention:

Example 1. Parenteral Delivery of Ampicillin, Stored in a Sorbitol/Glycerol Matrix as the Relatively Insoluble Acid Form, to a Parenteral Fluid Ampicillin is a commonly prescribed antibiotic that is usually delivered as the sodium salt because it is readily water soluble. However, the salt is unstable in solution and even to atmospheric moisture. The free acid form of ampicillin is more stable, but is so sparingly soluble as to be impractical for parenteral use.

100 parts by weight anhydrous sorbitol powder mixed with 1 part anhydrous glycerol was heated in an oven to 1500° C. The fluid melt was cooled to 50° C., at which time a dry powder mixture containing 20 parts sodium bicarbonate and 10 parts ampicillin acid was admixed therein and sample elements molded and allowed to harden. A formed element was placed in a simple flow chamber through which was pumped 0.9% sodium chloride at a rate of 100 mL/hr. Fluid samples collected at 2 min intervals were analyzed for ampicillin and sorbitol content. Ampicillin and sorbitol were delivered simultaneously over a 22 minute period (Table I). The collected solutions were free of any undissolved particles. Ampicillin in free acid form embedded in a sorbitol matrix has remained stable with no evidence or indication of degradation for a period of 2 months as of the date of this filing; in contrast to the sodium salt of ampicillin embedded in sorbitol which, analyzed by liquid chromatography, demonstrated 25% degradation.

TABLE I

| | Ampicillin Delivery from a Sorbitol Matrix | | | | | |
|---|---|---|---|---|---|---|
| Time: (min) | 2 | 6 | 10 | 14 | 18 | 22 |
| Ampicillin (Abs:$_{254\ nM}$) | 0.22 | 0.75 | 0.80 | 0.76 | 0.50 | 0.21 |
| Sorbitol (G/L) | 25 | 110 | 115 | 90 | 50 | 25 |

Example 2. Delivery of Acetylsalicylic Acid (Aspirin) from a Glucose Matrix Having Sodium Citrate Co-Dispersed Therein This is an example of a sparingly soluble drug that can be co-incorporated in a dry glucose matrix with a solubilizing agent that is also mutually reactive, yet it can be delivered in an undegraded state at the rate of matrix dissolution. 250 grams of dextrose monohydrate was boiled in water to 121° C. under vacuum of about two inches of mercury. After the melt cooled to 90° C., a well-mixed powder containing 78 grams of anhydrous sodium citrate and 55 grams of acetylsalicylic acid was dispersed in the viscous fluid and sample elements molded for testing.

When water flows over the formed element containing only aspirin, the glucose dissolves leaving behind an undissolved mass of aspirin. However, when the sodium titrate is co-dispersed in the matrix, the aspirin and the glucose dissolve simultaneously in stream of water flowing at 60 mL/hr as shown in Table II. Glucose Concentration was determined enzymatically in collected samples by glucose oxidase, and aspirin concentration was determined by light absorption at 297 nM. This mixture of aspirin and titrate is only possible under the dry conditions of the particulate composite formation, since aspirin reacts with citrate when they are heated together in the presence of significant amounts of water. Moreover, after dissolution the aspirin is recovered in a 98% acetylated state, as measured by liquid chromatography, further evidence of the mildness of the formation, storage and delivery steps as practiced.

TABLE II

Aspirin Delivery from a Glucose Matrix Containing Sodium Citrate as Solubilizing Species

| Time (Min) | 5 | 10 | 15 | 20 | 30 | 40 | 50 |
|---|---|---|---|---|---|---|---|
| Aspirin (% Dissolved) | 4.2 | 18.4 | 34.0 | 48.0 | 72.0 | 90.0 | 98.0 |
| Glucose (% Dissolved) | 5.0 | 20.0 | 34.0 | 50.0 | 75.0 | 92.0 | 99.0 |

Example 3. Dissolution Kinetics of Sorbitol Matrix Showing Dependence on Fluid Flow Rate To demonstrate the general delivery kinetics of this invention, pure sorbitol matrix elements were prepared by mixing 100 parts by weight dry sorbitol powder with 20 parts water and boiling to 95° C. The mixture was cooled to 80° C. and 1 part sorbitol powder admixed in the cooling melt, then sample elements 35 mM×32 mM×2.5 mM were molded for testing. A formed element sample was placed in a simple flow chamber through which was pumped 0.9% sodium chloride at rates from 20 to 1200 mL/hr. Fluid samples collected at timed intervals were analyzed for sorbitol content. As shown in Table III, $t_{90}$, the length of time required to deliver 90% of the sorbitol into the flowing stream, varied from 8 to 27 min, depending on the saline flow rate. The rate of sorbitol appearance in the flowing stream increases ($t_{90}$ decreases) with flow rate up to 200 mL/hr, then as flow rate is increased, delivery rate remains constant.

TABLE III

Dissolution kinetics of sorbitol matrix

| Flow Rate (ml/min) | 20 | 40 | 60 | 100 | 200 | 600 | 1200 |
|---|---|---|---|---|---|---|---|
| $t_{90}$ (min) | 26.7 | 19.3 | 14.6 | 11.9 | 8.8 | 8.8 | 9.1 |

Example 4. Bicarbonate Buffer in Sorbitol Matrix for Adjusting pH of Peritoneal Dialysis Solutions Peritoneal dialysis solutions are manufactured at acid pH to prevent degradation of glucose during sterilization. However, peritoneal infusion of acidic solutions is uncomfortable and may increase risk of infection. The present invention offers a means to neutralize the solutions in situ during delivery.

Solid sorbitol/bicarbonate elements were prepared by boiling sorbitol in water to 195° C., cooling to 45° C. and mixing in sodium bicarbonate powder, then molding sample elements. The elements were tested in flowing peritoneal dialysis solutions and were found to reproducibly modify the solution pH to 7. In initial storage tests at 25° and 45° C., the samples retained efficacy at 3 months.

Example 5. Controlled Administration of Dry Anticoagulant Preparation to Blood During Collection Blood collection sets currently contain pre-formulated anticoagulant solutions. This entails considerable cost increments for liquid handling, steam sterilization and transportation. A means to continually deliver, in a volume flow rate sensitive manner, the required amount of dry anticoagulant chemicals into each volume increment of blood as it flows from the phlebotomy needle through the collection set tubing into the collection bag would provide savings in product cost and provide the proper concentration of anticoagulant in the blood collected, independent of final volume. Moreover it would allow use of partial units of blood, which under present practice of drawing blood into a fixed volume of anticoagulant solution, contain excessive concentrations of the anticoagulant chemicals if insufficient blood is drawn into the collection bag.

A dry, solid, anhydrous particulate composition for anti-coagulating blood contained:

| Glucose | 44 Wt. % |
|---|---|
| Sodium Citrate | 46 |
| Citric Acid | 6 |
| Sodium Biphosphate | 4 |

The above glucose was dissolved as a near saturated solution in water by heating to boiling. Then, water was removed by boiling under a vacuum of about two inches of mercury and up to about 165° C., until the glucose reached the desired water content of about one weight percent. The viscous mass was then cooled in a manner to avoid crystallization, to obtain a supercooled solution. The other ingredients were added when the temperature of the molten glucose fell to about 95° C., with vigorous stirring, to form a homogeneous mass. The material was molded into lozenge shaped elements and allowed to solidify.

Samples were placed in a simple flow cell and water at 37° C. was passed through the cell at various flow rates chosen to cover the range experienced during blood collection. Glucose and titrate concentrations of collected samples were analyzed showing that delivery of anticoagulant was consistently flow dependent at the various flow rates; and that anticoagulant delivery reached completion with collection of a full unit volume (500 mL) at the various flow rates (Table IV).

TABLE IV

Dissolution Kinetics of Anticoagulant Composition

| Flow Rate (mL/min) | 50 | 70 | 100 |
|---|---|---|---|
| $t_{90}$ (min) | 9.6 | 7.0 | 5.0 |
| Volume collected (mL) | 480 | 490 | 500 |

We claim:

1. A method for delivering a controlled amount of at least one beneficial agent to a flowing medical fluid, said method comprising:

providing a formed element including a shaped solid matrix having at least one beneficial agent dispersed therein, the matrix comprising a water soluble, anhydrous sugar material, the formed element having a configuration selected so that upon introducing the formed element into a flowing stream of a medical fluid, the formed element dissolves at a dissolution rate selected to release the at least one beneficial agent into the medical fluid at a desired delivery rate;

providing a flow cell including a chamber connectible to a medical fluid administration line through which a medical fluid flows;

positioning the formed element in the chamber; and connecting the flow cell in the medical fluid administration line so that as a flowing stream of a medical fluid passes through the flow cell, the at least one beneficial agent is released into the medical fluid at the desired delivery rate.

2. The method of claim 1, wherein the sugar material is selected from the group consisting essentially of sugars, sugar alcohols and combinations thereof.

3. The method of claim 1, wherein the sugar material is selected from the group consisting essentially of glucose, fructose, mannose, lactose, sucrose, trehalose, sorbitol, mannitol, xylitol, glycerol, lycasin, dextran and combinations thereof.

4. The method of claim 1, wherein the sugar material is selected from monosaccharides or polymers having a degree of polymerization of about 1 or 2.

5. The method of claim 1, wherein the formed element has an elongate configuration.

6. The method of claim 1, wherein the flowing stream of medical fluid is a patient blood sample being collected in a collection bag.

7. The method of claim 1, wherein the flowing stream of medical fluid is a parenteral fluid being administered to a patient.

8. The method of claim 7, wherein the parenteral fluid is administered intravenously to the patient.

9. The method of claim 1, wherein the matrix further comprises a second beneficial agent and said formed element dissolves at a dissolution rate selected to release said second beneficial agent into said medical fluid at a desired second delivery rate.

10. The method of claim 1, wherein the formed element has an elongate, generally cylindrically shaped configuration.

11. The method of claim 10, wherein the formed element is visible in the flow chamber and the amount of said formed element remaining in the flow chamber provides a clear visual indication of the amount of the beneficial agent or agents that have been delivered.

12. The method of claim 1 wherein said beneficial agent is selected from the group consisting essentially of: antibiotics, aspirin, pH regulators, anti-coagulants, solubilizing agents and mixtures thereof.

13. An apparatus for delivering a controlled amount of at least one beneficial agent to a medical fluid provided in a medical fluid administration line, the apparatus comprising:

a flow cell including a chamber adapted to positionably receive a formed element therein;

a formed element positioned in said chamber, said formed element including a shaped solid matrix having at least one beneficial agent dispersed therein, said matrix comprising a water soluble, anhydrous sugar, the formed element having a configuration selected so that upon introducing a flowing stream of medical fluid through the chamber, the formed element dissolves at a dissolution rate selected to release the at least one beneficial agent into the medical fluid at a desired delivery rate; and means for connecting the flow cell in line in the medical fluid administration line to permit medical fluid to flow to said flow cell, through the chamber and out of the cell, whereby, the at least one beneficial agent is released by said apparatus into said medical fluid at said desired delivery rate.

14. The apparatus of claim 13 wherein the formed element is visible in the chamber and the amount of the formed element remaining in said flow chamber provides a clear visual indication of the amount of the at least one beneficial agent that has been delivered.

15. The apparatus of claim 13, wherein the sugar material is selected from the group consisting essentially of:

glucose, fructose, mannose, lactose, sucrose, trehalose, sorbitol, mannitol, xylitol, glycerol, lycasin, dextran and combinations thereof.

16. The apparatus of claim 13, wherein the at least one beneficial agent is selected from the group consisting essentially of: antibiotics, aspirin, pH regulators, anticoagulants, solubilizing agents and mixtures of any of the foregoing.

* * * * *